US012736599B2

(12) United States Patent
Erhardt et al.

(10) Patent No.: US 12,736,599 B2
(45) Date of Patent: Sep. 15, 2026

(54) IMPLANTABLE ARRAY WITH A REFERENCE STRUCTURE AND A METHOD OF IMAGING THE SAME

(71) Applicant: CorTec GmbH, Freiburg (DE)

(72) Inventors: Johannes Erhardt, Bad Bellingen (DE); Martin Schuettler, Emmendingen (DE); Thomas Stieglitz, Freiburg (DE)

(73) Assignee: CorTec GmbH, Freiburg (DE)

( * ) Notice: Subject to any disclaimer, the term of this patent is extended or adjusted under 35 U.S.C. 154(b) by 246 days.

(21) Appl. No.: 17/844,336

(22) Filed: Jun. 20, 2022

(65) Prior Publication Data

US 2022/0317211 A1 Oct. 6, 2022

Related U.S. Application Data

(63) Continuation of application No. PCT/EP2020/086885, filed on Dec. 17, 2020.

(30) Foreign Application Priority Data

Dec. 19, 2019 (EP) .................................... 19218177

(51) Int. Cl.

*G01R 33/28* (2006.01)
*A61B 5/00* (2006.01)

(Continued)

(52) U.S. Cl.

CPC ............ *G01R 33/287* (2013.01); *A61B 5/055* (2013.01); *A61B 5/062* (2013.01); *A61B 5/6847* (2013.01); *G01R 33/50* (2013.01); *A61B 2560/0406* (2013.01); *A61B 2560/0468* (2013.01); *A61B 2562/046* (2013.01); *A61B 2562/164* (2013.01)

(58) Field of Classification Search

CPC .................. G01R 33/287; G01R 33/50; G01R 33/56536; G01R 33/286; G01R 33/5602; A61B 5/062; A61B 5/6847; A61B 2560/0406; A61B 2560/0468;

(Continued)

(56) References Cited

U.S. PATENT DOCUMENTS 5,123,422 A 6/1992 Charvin
9,592,377 B2 * 3/2017 Greenberg ......... A61N 1/37229

(Continued)

FOREIGN PATENT DOCUMENTS

CN 109700453 A 5/2019

OTHER PUBLICATIONS

Dorne, L. et al. 1994. Magnetic Resonance Study of Virgin and Explanted Silicone Breast Prostheses. ASAIO Journal. M625-M631 (Year: 1994).*

(Continued)

*Primary Examiner* — Anh Tuan T Nguyen
*Assistant Examiner* — Dean N Edun
(74) *Attorney, Agent, or Firm* — Myers Wolin, LLC

(57) ABSTRACT

An implantable array suitable for being placed in anatomic tissue of a human or animal body is provided. The implantable array has a substrate and a reference structure, the reference structure being formed by a number of notches arranged in at least one outer edge of the substrate, the reference structure defines a spatial relationship with predefined points of the array.

4 Claims, 3 Drawing Sheets

(51) Int. Cl.
*A61B 5/055* (2006.01)
*A61B 5/06* (2006.01)
*G01R 33/50* (2006.01)

(58) Field of Classification Search
CPC ........ A61B 2562/046; A61B 2562/164; A61B 5/055; A61B 2562/08; A61B 5/064
See application file for complete search history.

(56) References Cited

U.S. PATENT DOCUMENTS

2012/0277834 A1* 11/2012 Mercanzini ........ A61N 1/36125 607/116
2016/0033602 A1* 2/2016 Fritz .................. G01R 33/4816 324/309
2016/0120457 A1 5/2016 Wu et al.
2017/0252555 A1 9/2017 Greenberg et al.
2017/0303815 A1* 10/2017 De Limon ............. A61B 5/086
2018/0078386 A1 3/2018 Kieser et al.
2018/0085186 A1 3/2018 Kieser et al.
2018/0292494 A1 10/2018 Tamir et al.
2018/0369574 A1 12/2018 Dubuclet et al.
2019/0056470 A1* 2/2019 Wang ................. G01R 33/5601
2019/0308008 A1* 10/2019 Kryzanski ............ A61N 1/0529

OTHER PUBLICATIONS

Salam, M. et al. 2014. Subdural porous and notched mini-grid electrodes for wireless intracranial electroencephalographic recordings. Journal of Multidisciplinary Healthcare, 2014:7, 573-586 (Year: 2014).*

International Search Report issued by the European Patent Office for International Patent Application No. PCT/EP2020/086885, mailed Feb. 25, 2021.

The extended European search report and European search opinion issued by the European Patent Office for European Patent Application No. 19218177.4, dated Jul. 2, 2020.

Salam et al. "Subdural porous and notched mini-grid electrodes for wireless intracranial electroencephalographic recordings", Journal of Multidisciplinary Healthcare, 2014, pp. 573-586, Dove Medical Press Limited.

Office Action issued by the Chinese Intellectual Property Administration for Chinese Patent Application No. 202080082302.1, mailed on Mar. 4, 2025, with search report and machine-generated English translation of Office Action attached.

* cited by examiner

IMPLANTABLE ARRAY WITH A REFERENCE STRUCTURE AND A METHOD OF IMAGING THE SAME

CROSS REFERENCE TO RELATED APPLICATIONS

This application is a continuation of International Application No. PCT/EP2020/086885, filed Dec. 17, 2020, which claims priority to European Patent Application No. 19218177.4, filed Dec. 19, 2019, the contents of each of which are incorporated by reference herein.

FIELD OF THE INVENTION

The present invention relates to an implantable array with a reference structure which is visible in magnetic resonance images (MRI) when the array is implanted for example in a human or animal body, and to a method of imaging the electrode array.

BACKGROUND

Such an array may be an electrode array which is implanted on the surface of the brain e.g., for pre-surgical assessment of cortical electrical activity in patients with epilepsy.

Hereby, MRI is used to localize the electrode contacts of the implanted electrode array with respect to the anatomy of the patient. However, metal components or other good electric current conductive materials like carbon and electric conductive polymers may cause MRI artifacts that compromise the results especially in the direct vicinity of these components and materials.

Thin-film implants which may feature 100× less metal thickness may mitigate these artifacts, but thin-film implants produce inconspicuous MRI signal voids in many clinical MRI sequences, and are therefore not suitable for localizing the electrode with MRI. Very small metal contacts or very thin metal layers may not become visible in clinical MRI at all.

But imperatively, physicians need to know the implant position, and the value of intracranial EEG increases with the precision of electrode localization.

SUMMARY

The present invention is directed towards a problem to provide an implantable array for MRI-based localization of its standard or micro-sized planar electrode contacts, and a method of MR-imaging such an array.

This problem may be solved by the implantable array and the method of imaging an implantable array according to the claims.

Accordingly, provided is an implantable array suitable for being placed in anatomic tissue of a human or animal body, comprising a substrate, and a reference structure, the reference structure being formed by a number of notches arranged in at least one outer edge of the substrate, the reference structure defining a spatial relationship with predefined points of the array.

Advantageous embodiments of the invention may comprise the following features.

The notches may be arranged in at least two adjacent outer edges of the array.

Each notch may be spaced apart from each other notch.

The spatial relationship may be over a surface of the array.

The grid may be a rectangular, regular grid.

The location may be at least one of an electrode contact, a fluidic interface, a point of geometrical significance.

The implantable array may comprise at least one layer of a polymer, in particular selected from the group comprising silicone rubber, polyurethane, polyimide, epoxy, liquid crystal polymer, and parylene.

The array may be an electrode array.

The array may be a planar and flexible array.

Provided is also a method of magnetic resonance imaging, MRI, of the implantable array according to one of the preceding claims, when implanted in a human or animal body, the method comprising

- acquiring at least one first T2-weighted image of a body region comprising the implantable array, and at least one second T2-weighted image of the body region comprising the implantable array,
- the first image being acquired at a first echo time, TE_1, the first echo time being smaller than the transverse relaxation time, T2*, of silicone,
- the second T2-weighted image being acquired at a second echo time, TE_2, the second echo time being selected to be equal to or greater than the transverse relaxation time, T2*, of the substrate, but smaller than the transverse relaxation time of body tissue,
- generating a difference image on the basis of the at least one second image and the at least one first image,
- wherein the first sequence and the second sequence comprise identical relaxation time, TR, inversion time, TI, and flip angle ($\alpha$) setting.

Hereby, the at least one and second images may be acquired on the basis of first and second predetermined gradient echo sequences.

BRIEF DESCRIPTION OF THE DRAWING

The invention and embodiments thereof will be described below in further detail in connection with the drawing.

DETAILED DESCRIPTION OF THE PREFERRED EMBODIMENTS

Figure 1:
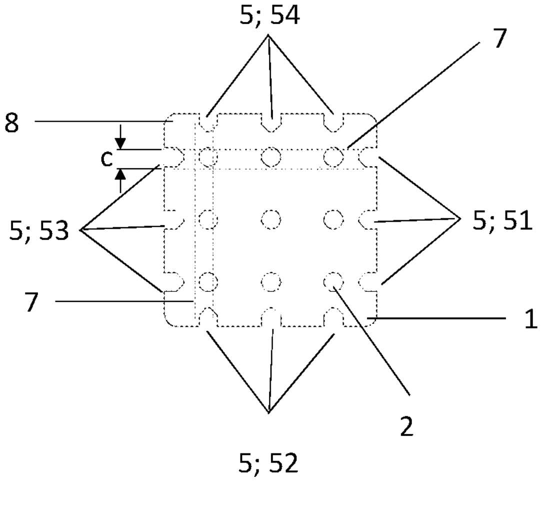
FIG. 1 illustrates schematically the implantable electrode array according to an embodiment of the invention.
Figure 2:
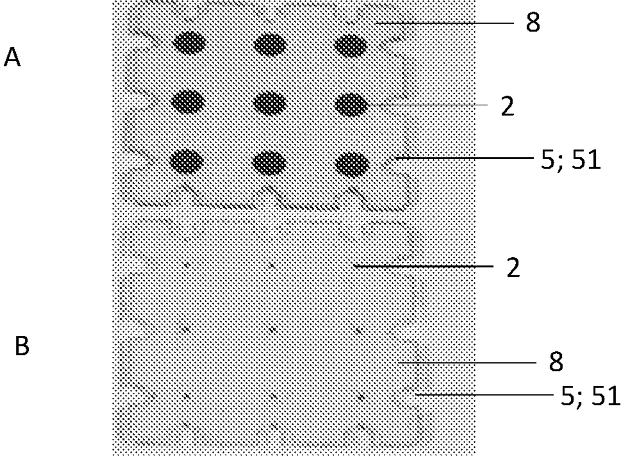
FIG. 2 illustrates the implantable electrode array according to embodiments of the invention.

FIG. 1 and FIG. 2 illustrate embodiments of the implantable array, that is a planar implantable electrode array. The implantable electrode array comprises at least one substrate 1 made from a biocompatible polymer. The polymer can be selected from the group comprising silicone rubber, polyurethane, polyimide, epoxy, liquid crystal polymer, and parylene.

The implantable electrode array is preferably flexible such that it can adapt its form to the form of the location in the cortex of a human or animal where it is placed. The electrode array comprises sensor electrode contacts 2 of diameter c on its surface 8. The sensor contacts are equidistant to each other, and are arranged in columns and rows, i.e., they define a regular rectangular grid over the surface of the electrode array.

Figure 3:
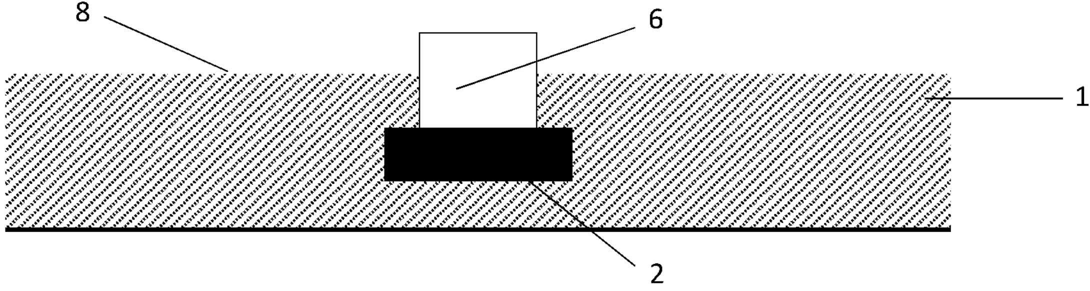
FIG. 3 illustrates sectional view of the implantable electrode array according to an embodiment of the invention.

The electrode contacts 2 may be located in apertures 6 in the polymer 1 of a diameter smaller than diameter c, refer to FIG. 3. Typical diameters c of the electrode contacts 2 are 4 mm. The apertures 6 may have a diameter of 2.3 mm, refer to FIG. 2A. Typical electrode arrays may comprise e.g. 3×3 electrode contacts or 3×6 electrode contacts, depending on the intended application. A typical spacing between two electrode contacts 2 (interelectrode spacing) may be 10 mm. Microelectrode arrays, according to a further embodiment of the invention, may have contacts 4 with diameters of about 0.3 mm, refer to FIG. 2B.

Additionally to, or instead of the contacts 2, other predefined points of interest on the implant array may be referenced via the reference structure. Thus, most generally, the predefined points 2 which can be referenced by the patterns 51, 52, 53, 54, 55 may be a) electrical contacts 2, i.e., sensor contacts, whose material may be selected from metal, conductive polymer, carbon on the implantable array, as described above, b) fluidic interfaces (e.g., inlets or outlets for conveying liquids into the body, or out of the human or animal body), c) other points of particular geometrical significance for the physician.

The implantable electrode array further comprises a reference structure 5. The reference structure 5 is formed by notches 51, 52, 53, 54 along the four outer edges of the substrate 8 of the electrode array. The notches 51, 52, 53, 54 are distinct from each other and regularly spaced apart from each other. Each of these notches is concavely formed, i.e., forms a recess in the respective outer edge towards the inner of the array. All the notches 51, 52, 53, 54 have identical shape.

The notches 51, 52, 53, 54 are located at positions on straight elongated lines 7 through the contacts 2. The dimension of the notches may be the same as the diameter of the contacts.

In other words, the reference structure 5, i.e., the notches 51, 52, 53, 54 define a spatial relationship with the electrode contacts 2 of the implant array. The spatial relationship is a regular, rectangular grid 7 over a surface 8 of the array, wherein the electrode contacts are in the crossings of the grid lines.

In MRI of the electrode array, the edges thereof with the notches 51, 52, 53, 54 are visible, as long as the substrate 8 of the electrode array is visible. Since the notches 51, 52, 53, 54 define a grid over the surface 8 of the electrode array comprising the electrode contacts 2, the positions of the sensor contacts 2 can be determined as being located at the (imaginary) crossing points of the (imaginary) grid lines in the MRIs. Therefore, the notches 51, 52, 53, 54 can be used as reference structure 5 for localizing the electrode contacts 2 (or the other points of interest) in the MRIs, regardless whether or not the electrode contacts 2 themselves are correctly imaged in the MRIs.

In the following, the method of magnetic resonance imaging, MRI, of the implantable electrode array as described before, implanted in a human or animal body is outlined.

Hereto, T2-star (T2*=effective transverse relaxation time) weighted images are used, especially acquired with Gradient Echo (GRE) imaging sequences.

The substrate material (e.g., silicone) has a very short T2* at the clinical field strengths that are typically used for MRI (e.g., B=0.2 Tesla to 3.0 Tesla) of about 1-2 ms or less. The MRI signal S in Gradient Echo imaging (GRE) is given by S(TE; T2*)=S_0*EXP(−TE/T2*), where TE is the variable echo time, and S_0 is the signal at a (fictitious) echo time TE=0 ms. On the other hand, most tissues have T2* which are longer than 2 ms, so that the factor EXP(−TE/T2*) for them does not vary much, if TE is varied in the range of 0.5-2 ms, whereas for silicone the signal at a TE_1 of 1-2 ms is much lower as compared to a TE_2 of 0.5 ms or less. Thus, the signal difference $$\text{Delta\_S} = S(\text{TE\_1}) - S(\text{TE\_2}) = \text{S\_0}^*\left(\text{EXP}(-\text{TE\_1}/T2^*) - \text{EXP}(-\text{TE\_2}/T2^*)\right)$$

is non-vanishing for the substrate (e.g., silicone), but it does vanish for brain tissue.

A marker from substrate material (e.g. silicone) can thus be selectively visualized in a difference image acquired with two different echo times, where one is less than the T2* of the substrate material (e.g., silicone), and the other is of the order or slightly larger than the substrate (silicone) T2*, but still lower than that of normal (brain) tissue.

Thus, the method comprises the steps of:

Acquiring at least one first T2-weighted image of a body region comprising the implantable array, and at least one second T2-weighted image of the body region comprising the implantable array;

the first image being acquired at a first echo time, TE_1, the first echo time being smaller than the transverse relaxation time, T2*, of the substrate material (silicone);

the second T2-weighted image being acquired at a second echo time, TE_2, the second echo time being selected to be equal to or greater than the transverse relaxation time, T2*, of the substrate material (silicone), but smaller than the transverse relaxation time, T2*, of body tissue;

generating a difference image on the basis of the at least one second image and the at least one first image.

The at least one first and second images are acquired on the basis of first and second predetermined Gradient Echo (GRE) sequences.

Herein, the first sequence and the second sequence comprise identical relaxation time TR, inversion time TI, and flip angle (α) setting.

What is claimed is:

1. An implantable electrode array suitable for being placed in anatomic tissue of a human or animal body, comprising:

a substrate comprising a plurality of notches in at least two adjacent outer edges of the substrate of the electrode array; and a plurality of electrode contacts at a surface of the substrate, wherein each notch of the plurality of notches defines a corresponding grid line extending in a direction perpendicular to the edge in which the corresponding notch is located, each grid line passing through the corresponding notch, and wherein the grid lines form a rectangular grid over the surface of the substrate, and wherein the electrode contacts are at cross points defined by two of the grid lines, so that the plurality of notches define locations of the electrode contacts of the electrode array in MRI images.

2. The implantable electrode array of claim 1, wherein each notch of the plurality of notches is spaced apart from each other notch of the plurality of notches.

3. The implantable electrode array of claim 1, wherein the implantable electrode array comprises at least one layer of a polymer selected from the group consisting of polyurethane, polyimide, epoxy, liquid crystal polymer, and parylene.

4. The implantable electrode array of claim 1, wherein the electrode array is a planar and flexible array.

* * * * *